(12) United States Patent
Sumanaweera et al.

(10) Patent No.: US 11,097,127 B2
(45) Date of Patent: *Aug. 24, 2021

(54) HEART TISSUE SURFACE CONTOUR-BASED RADIOSURGICAL TREATMENT PLANNING

(71) Applicant: Varian Medical Systems, Inc., Palo Alto, CA (US)

(72) Inventors: Thilaka Sumanaweera, Los Altos, CA (US); Ed Gardner, San Jose, CA (US); Oliver Blanck, Bad Oldesloe (DE); Tao Cai, Sunnyvale, CA (US); Darrin Uecker, Sunnyvale, CA (US); Patrick Maguire, Menlo Park, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/194,751

(22) Filed: Nov. 19, 2018

(65) Prior Publication Data

US 2019/0351254 A1 Nov. 21, 2019

Related U.S. Application Data

(63) Continuation of application No. 15/357,804, filed on Nov. 21, 2016, now abandoned, which is a
(Continued)

(51) Int. Cl.
*A61N 5/10* (2006.01)
*A61B 34/10* (2016.01)
(Continued)

(52) U.S. Cl.
CPC ............ *A61N 5/1039* (2013.01); *A61B 6/032* (2013.01); *A61B 6/503* (2013.01); *A61B 6/5211* (2013.01); *A61B 34/10* (2016.02); *A61N 5/103* (2013.01); *G06T 15/08* (2013.01); *G06T 19/20* (2013.01); *A61B 2034/104* (2016.02);
(Continued)

(58) Field of Classification Search
CPC .. A61B 6/00; A61B 5/05; A61B 19/50; A61N 5/103
USPC .................... 600/1, 427, 443, 439; 128/916; 250/492.1–492.3; 378/4–20, 64–69, 108, 378/163–165; 382/103, 108
See application file for complete search history.

(56) References Cited

U.S. PATENT DOCUMENTS 5,687,737 A 11/1997 Branham et al.
6,118,847 A 9/2000 Hernandez-Guerra et al.
(Continued)

*Primary Examiner* — John P Lacyk
(74) *Attorney, Agent, or Firm* — Duane Morris LLP; Manita Rawat

(57) ABSTRACT

A system that generates a three-dimensional model of a tissue surface, for example the inner surface of the heart from two-dimensional image data slices. On this surface, one or more pattern lines are drawn, e.g., by a physician using a user interface, to designate desired lesion(s) on the surface. From the pattern lines, a three-dimensional volume for a lesion can be determined using known constraints. Advantageously, the series of boundaries generated by the three-dimensional volume may be projected back onto the individual CT scans, which then may be transferred to a standard radiosurgical planning tool. A dose cloud may also be projected on the model to aid in evaluating a plan.

22 Claims, 16 Drawing Sheets

Related U.S. Application Data continuation of application No. 14/930,419, filed on Nov. 2, 2015, now Pat. No. 9,504,853, which is a continuation of application No. 12/838,308, filed on Jul. 16, 2010, now Pat. No. 9,205,279.

(60) Provisional application No. 61/226,613, filed on Jul. 17, 2009.

(51) Int. Cl.
 *A61B 6/03* (2006.01)
 *A61B 6/00* (2006.01)
 *G06T 15/08* (2011.01)
 *G06T 19/20* (2011.01)

(52) U.S. Cl.
 CPC ... *A61B 2034/105* (2016.02); *A61B 2034/107* (2016.02); *G06T 2210/41* (2013.01)

(56) References Cited

U.S. PATENT DOCUMENTS

| | | |
|---|---|---|
| 6,443,894 B1 | 9/2002 | Sumanaweera et al. |
| 6,778,850 B1 | 8/2004 | Adler et al. |
| 6,889,695 B2 | 5/2005 | Pankratov |
| 6,913,603 B2 | 7/2005 | Knopp et al. |
| 7,171,257 B2 | 1/2007 | Thomson |
| 7,756,567 B2 | 7/2010 | Kuduvalli et al. |
| 9,205,279 B2 | 12/2015 | Sumanaweera et al. |
| 9,504,853 B2 | 11/2016 | Sumanaweera et al. |
| 2004/0131150 A1 | 7/2004 | Pankratov et al. |
| 2006/0009759 A1 | 1/2006 | Chrisitian et al. |
| 2007/0014452 A1 | 1/2007 | Suresh et al. |
| 2007/0032826 A1 | 2/2007 | Schwartz |
| 2008/0317204 A1 | 12/2008 | Sumanaweera et al. |
| 2009/0180589 A1 | 7/2009 | Wang et al. |
| 2010/0183121 A1 | 7/2010 | Riker et al. |

HEART TISSUE SURFACE CONTOUR-BASED RADIOSURGICAL TREATMENT PLANNING

CROSS-REFERENCES TO RELATED APPLICATIONS

This application is a continuation of U.S. patent application Ser. No. 15/357,804, filed Nov. 21, 2016, is a continuation of U.S. patent application Ser. No. 14/930,419, filed Nov. 2, 2015, which is a continuation of U.S. patent application Ser. No. 12/838,308, filed Jul. 16, 2010, which claims the benefit of U.S. Provisional Application No. 61/226,613, filed on Jul. 17, 2009, which is incorporated herein by reference in their entirety for all purposes.

BACKGROUND

Tumors and other targets in the head, spine, abdomen, and lungs have been successfully treated using radiosurgery. During radiosurgery, a series of beams of ionizing radiation are often directed from outside a patient so as to converge at a target region, with the radiation beams often comprising MeV X-ray beams fired from different positions and orientations. The beams can be directed through intermediate tissue toward the target tissue so as to alter the biology of a tumor. The beam trajectories help limit the radiation exposure to the intermediate and other collateral tissues, while the cumulative radiation dose at the target can treat the tumor. The CYBERKNIFE radiosurgical system (Accuray Inc.) and the TRILOGY radiosurgical system (Varian Medical Systems) are two known radiosurgical treatment systems.

Modern radiosurgical systems incorporate imaging into the treatment system so as to verify the position of the target tissue and adjust to minor patient movements. Some systems also have an ability to treat tissues that move during respiration, and this feature has significantly broadened the number of patients that can benefit from radiosurgery.

Radiosurgical treatments of other tissues that undergo physiological movements have also been proposed, including the directing of radiation toward selected areas of the heart for treatment of atrial fibrillation and other arrhythmias. During atrial fibrillation, the atria lose their organized pumping action. In a healthy sinus rhythm, the atria contract, the valves open, and blood fills the ventricles or lower chambers. The ventricles then contract to complete an organized cycle of each heartbeat. Atrial fibrillation, in contrast, has been characterized as a storm of electrical energy that travels across the atria causing the upper chambers of the heart to quiver or fibrillate. During atrial fibrillation, the blood is not able to empty sufficiently from the atria into the ventricles with each heartbeat. By directing ionizing radiation toward the heart based on appropriate lesion patterns, the resulting scar tissue may prevent recirculating electrical signals and thereby diminish or eliminate the atrial fibrillation.

In standard radiosurgical treatments of tumors and the like, computed tomography (CT) imaging provides a series of planar X-ray scans. For the X-rays adjacent a tumor, the planning physician draws a boundary of the target tissue, with the boundary being drawn on the scan traversing through the tumor and the boundary encompassing the tumor (and typically including some additional offset or margin of treated tissue for safety). As the tumor is typically contained within one organ (but may alternatively extend beyond the organ surface to an adjacent organ) the planned treatment boundary is fairly independent of tissue/tissue interface contours. Hence, the treatment plan is typically drawn up as a series of circles surrounding the tumor on each CT scan in which the tumor is visible.

It is difficult to draw an appropriate arrhythmia lesion treatment plan for forming patterns on conventional planar CT scans using standard radiosurgical planning interfaces. A physician must evaluate the multiple CT scans, and draw appropriate lines and/or circles representing a treatment plan at each planar slice of the heart. The physician must be able to visualize desired treatment areas from each planer scan. While this appears to be a mere inconvenience, work in connection with the present invention indicates it is surprisingly difficult to efficiently establish an arrhythmia treatment plan using existing radiosurgical treatment planning tools in light of the geometry of the heart.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

In accordance with an embodiment, a system generates a three-dimensional model of a tissue surface of the heart, and specifically of the inner surface (the blood/heart tissue interface). On this surface, one or more pattern lines are drawn, e.g., by a physician using a user interface, to designate desired lesion(s) on the surface for inhibiting contractile pathways. From the pattern lines, a three-dimensional volume for a lesion can be determined using known constraints (such as providing sufficient thickness from the inner heart tissue for the lesion to extend throughout the heart wall, providing sufficient width to prevent propagation of contractions across the lesion, and the like). Advantageously, the series of boundaries generated by the three-dimensional volume may be projected back onto the individual CT scans, which then may be transferred to a standard radiosurgical planning tool.

The radiosurgical planning tool may use existing trajectory calculation routines to generate a radiosurgical plan having several radiosurgical trajectories, or contours. Once the trajectories have been identified to form the desired lesion, a "dosage cloud" can be output to the new planning tool with the display providing an area at the tissue surface (e.g., the blood/heart tissue interface) which will receive sufficient radiation to form a lesion.

To facilitate planning of the radiosurgical treatment, the physician will typically identify locations graphically on the three-dimensional tissue surface, with points and lines snapping to the model of the tissue surface. The output lesion indication may be calculated as a simple isodose contour along the tissue surface.

In an embodiment, a radiosurgical method is provided for treating a patient body having a heart, the heart having a non-tumerous disease. The method includes acquiring three dimensional image data from the heart; generating a three dimensional model of a tissue surface of the heart utilizing the image data; receiving user input on the surface model of a desired ionizing radiation treatment lesion pattern for mitigating the disease; and outputting information regarding a planned lesion pattern relative to the three dimensional image data based upon the desired lesion pattern.

Generating the three dimensional model may include generating a model of the heart based upon a boundary between blood and tissue of the heart. The boundary may be, for example, an inner surface of the heart tissue.

The three dimensional image data from the heart may be a plurality of slices of two dimensional data. Generating the three dimensional model may include generating a model of the heart based upon segments of the boundary between the blood and the heart tissue in each slice of the two dimensional data. The three dimensional model may be formed, for example, by stacking or assembling together the segments, and by extending the surface between the segments. In an embodiment, outputting includes projecting the lesion pattern onto each of the plurality of slices of two dimensional data.

A three-dimensional volume for a lesion may be generated based upon the user input, and the information may be generated based upon the three-dimensional volume. The volume may be generated, for example, by expanding the user input to a width that is sufficient to inhibit contractile pathways, expanding the user input to a depth that is sufficient to transmurally penetrate through the tissue of the heart, or expanding the user input to cover an area of tissue of interest at which the treatment is to occur.

In accordance with another embodiment, a radiosurgical method is provided for treating a patient body having a heart, the heart having a non-tumerous disease. The method includes acquiring three dimensional image data from the heart; generating a three dimensional model of a tissue surface of the heart utilizing the image data; receiving user input on the surface model of a desired ionizing radiation treatment lesion pattern for mitigating the disease; and generating a ionizing radiation treatment plan based upon the desired lesion pattern, and projecting a dose cloud relative to the image data based upon the desired treatment plan.

The method may further include snapping the user input for the lesion pattern to the surface of the model. The dose pattern may be evaluated with respect to the user input to determine sufficient treatment which may, for example, involve walking the dose pattern around the surface to confirm that the loop forms a complete circle around the surface. Walking may involve evaluating a thickness of the loop with respect to a threshold.

In accordance with another embodiment, a radiosurgical system is provided for treating a patient body with a heart, the heart having a non-tumerous disease. The system includes an image capture device for acquiring three dimensional planning image data from the heart; and a processor system comprising a modeling module coupled to the image data for generating a surface model of the heart based upon the image data, and an input for identifying a target region of the heart on the surface model, the processor system coupling the input to the modeling module so generate a lesion pattern on the image data in response to the input on the surface model.

In accordance with still another embodiment, a radiosurgical system is provided for treating a patient body with a heart, the heart having a non-tumerous disease. The system includes an image capture device for acquiring three dimensional planning image data from the heart; a radiation source for transmitting a plurality of beams of ionizing radiation from outside the body; and a processor system that includes a planning module having an input for identifying a target region of the heart, the planning module generating a plan of the radiation beams in response to the target region and the planning image data and to project a dose cloud based upon the plan, and a modeling module coupled to the image data for generating a surface model of the heart based upon the image data, the processor system coupling the planning module to the modeling module to project the dose cloud onto the surface model.

For a fuller understanding of the nature and advantages of the present invention, reference should be made to the ensuing detailed description and accompanying drawings.

DETAILED DESCRIPTION OF THE INVENTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Embodiments herein are directed to radiosurgical treatment planning. Some described embodiments are directed to radiosurgical planning for treatment of a non-tumor disease of the heart and/or coronary vessels, but the features described herein are not limited to that context.

Figure 1:
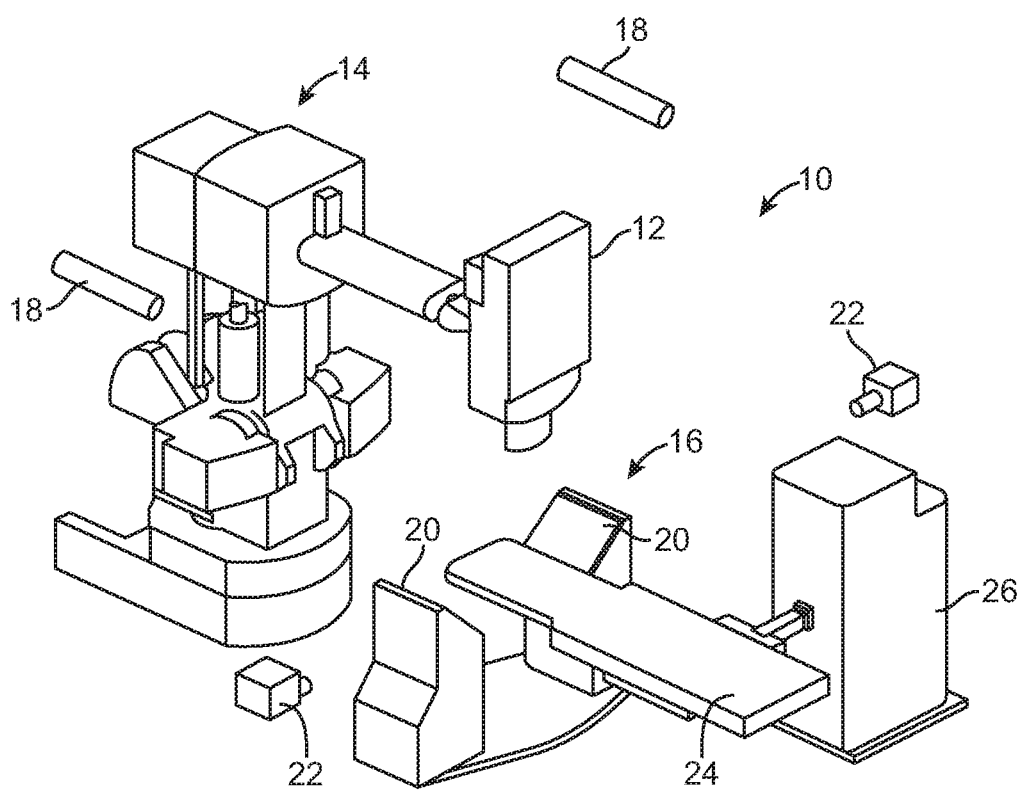
FIG. 1 illustrates an exemplary modified stereotactic radiosurgery system that may be utilized with embodiments.

The radiosurgical treatment planning described herein may take advantage of many components included in or derived from known radiation delivery systems. As an example, an exemplary modified CYBERKNIFE stereotactic radiosurgery system 10 is illustrated in FIG. 1. Radiosurgery system 10 includes a lightweight linear accelerator 12 mounted to a robotic arm 14. An image guidance system 16 includes biplane diagnostic X-ray sources 18 and image detectors 20 so as to enhance registration between robot arm 14 and the target site. As the tissues in the target region may not present a high-contrast image, image guidance system 16 may use image processing techniques to identify the location of one or more surrogate structures, with the surrogates typically including a high-contrast natural tissue structure (such as a bone or the like) or an artificial implanted fiducial marker that moves in correlation with the target tissue. Target tracking may also make use of one or more surface image cameras 22, particularly for identifying movement of the chest wall corresponding to respiration. Cameras 22 may monitor light emitting diodes (LEDs) or other high-contrast fiducial markers visible on the patient's chest. A patient support 24 is movably supported by an alignment arm 26 so as to facilitate bringing the patient (and treatment site) into alignment with robot arm 14.

Figure 2:
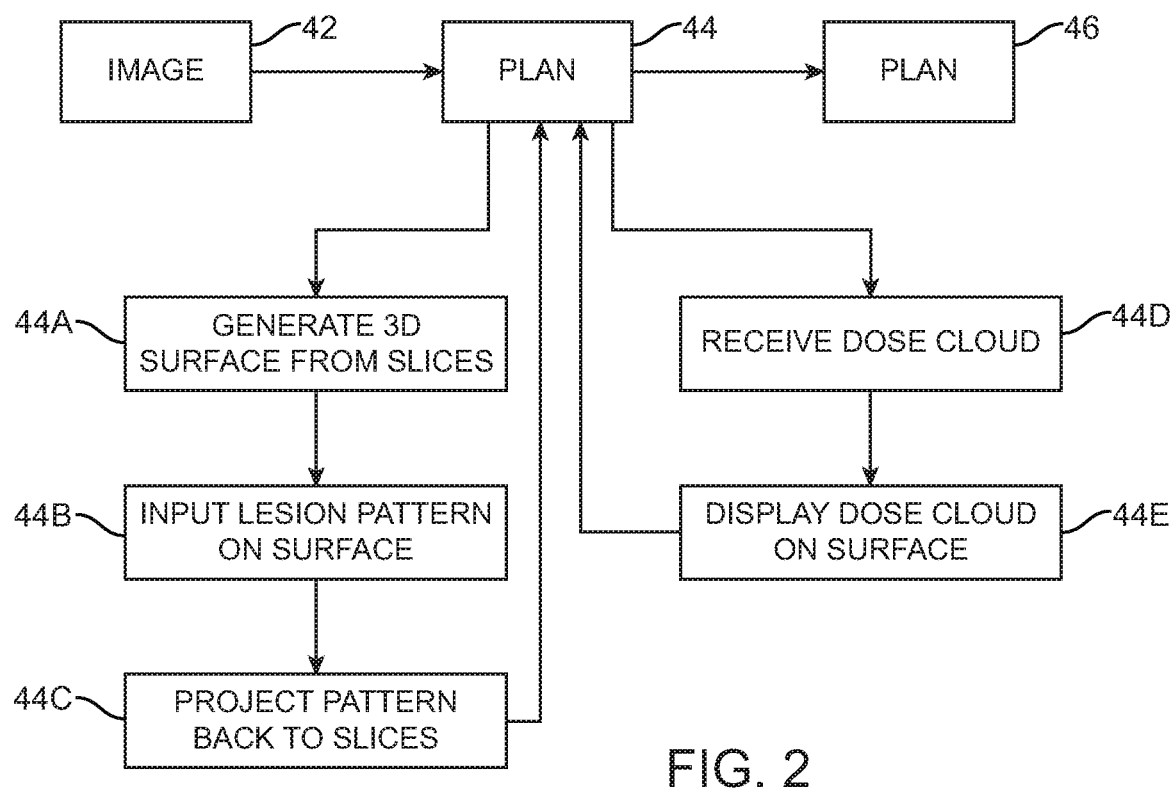
FIG. 2 is a flowchart representing a method of radiosurgical treatment according to embodiments.

Referring now to FIG. 2, a relatively simple treatment flowchart 40 can represent a method used before and during radiosurgical treatment according to embodiments of the present invention. The internal tissues are imaged 42 for planning purposes, typically using a remote imaging modality such as a computed tomography (CT), magnetic resonance imaging (MRI), ultrasound imaging, X-ray imaging, optical coherence tomography, a combination of these, or other imaging modalities. Note that the tissue structure which will actually be targeted for radiation remodeling need not necessarily be visible in the image, so long as sufficiently contrasting surrogate structures are visible in the image data to identify the target tissue location. The planning imaging used in many embodiments will include a time sequence of three-dimensional tissue volumes, with the time sequence typically spanning one or more movement cycles (such as a cardiac or heartbeat cycle, a respiration or breathing cycle, and/or the like). In exemplary embodiments, the image data comprises a series of CT slices through the heart so as to provide volumetric or three-dimensional image data. The time series of three-dimensional heart images are preferably acquired at times that are distributed throughout the heartbeat cycle, so that the image planning data effectively comprises a time series of three-dimensional image datasets providing information regarding the motion of cardiac tissues during the heartbeat.

Based on the imaging data obtained from imaging 42, a plan 44 can be prepared for treatment of the tissue at the target site. After completion of plan 44, radiosurgical treatment 46 of the heart may be initiated by positioning the patient on patient support 24, bringing the patient into alignment with robot arm 14, and directing the planned series of radiation beams from the linear accelerator 12 to the target region of the heart.

Embodiments herein are directed to systems and methods that aid in development of the plan 44, which may be used with existing or newly developed imaging 42 and treatment 46. However, one advantage of the plan 44 defined herein is that it may be used with existing imaging, such as the CT imaging described above, and with conventional radiosurgical planning tools, such as the MULTIPLAN planning tool (Accuray, Inc.). Imaging, for example, may take the forms described above, or other forms, but in embodiments utilizes conventional series of slices (e.g., CT slices) through the heart so as to provide volumetric or three-dimensional image data. Treatment 46 may be conventional or modified, and one embodiment is described in concurrently filed U.S. Patent Application No. 61/271,177 entitled, "Heart Treatment Kit, System, and Method for Radiosurgically Alleviating Arrhythmia", the full disclosure of which is incorporated herein by reference.

Treatment plan 44 typically comprises a target region and a series of radiation beams which intersect within the target region. The radiation dose within the target tissue should be at least sufficient to provide the desired lesions. Typically, the radiation dose will be sufficient to ablate tissue, inhibit contractile pathways within the heart, inhibit arrhythmogenesis, and/or the like. Radiation dosages outside the target tissue will preferably decrease with a relatively steep gradient so as to inhibit excessive damage to collateral tissues, with radiation dosages in specified sensitive and/or critical tissue structures often being maintained below a desired maximum threshold to avoid deleterious side effects.

Figure 3:
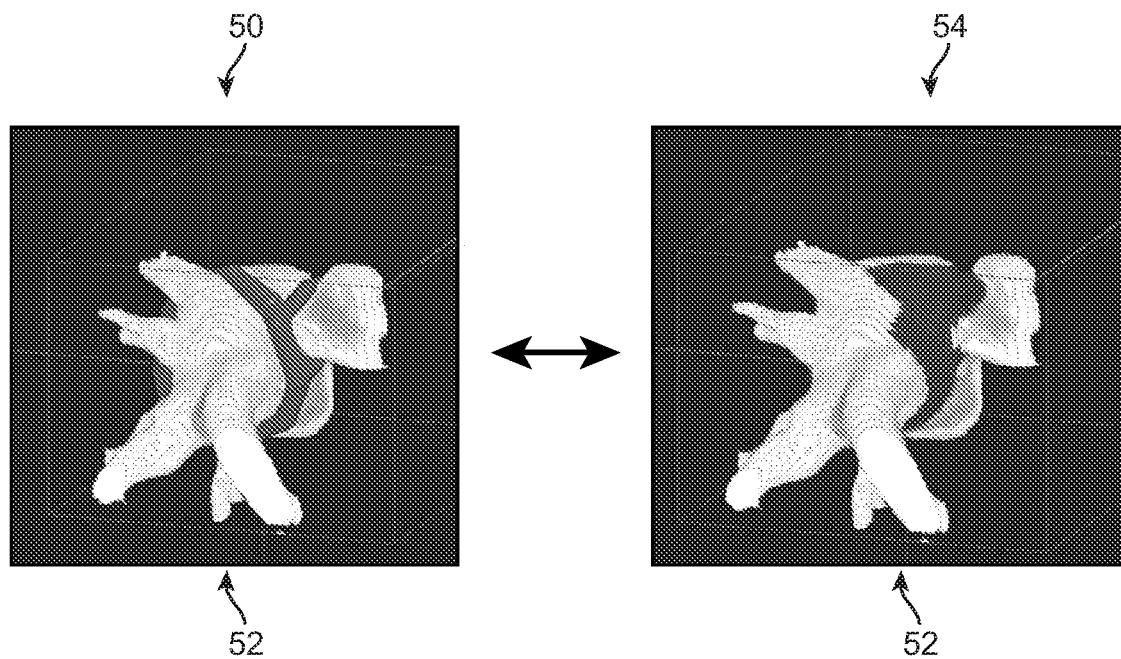
FIG. 3 is a representation of a three dimensional model of a heart surface, with a lesion plan added on a left view, and a dose cloud added on a right view, in accordance with embodiments herein.

Referring now to FIGS. 2 and 3, broadly described, an exemplary treatment planning module generates 44A a 3D model of a surface 52 (FIG. 3), generally from CT slices, although other imaging data may be used. A user interface allows the system user to input 44B a desired lesion pattern 50 (FIG. 3) with reference to a surface of a tissue, in the example shown in the drawings, the surface 52 of a heart. For treatment of moving tissues of the heart so as to inhibit arrhythmias, the reference heart surface 52 may comprise the blood/tissue interface or the inner surface of one or more heart chambers and adjacent blood vessels. Alternative embodiments may employ an outer surface of the heart as the reference surface, although the inner surface may be more easily identified from the three-dimensional planning image data by introducing imaging contrast agent during the image acquisition step 42. Thus, there is a clear demarcation between the tissue and the blood, allowing for a more precise definition of the surface 52. The lesion pattern 50 is used in part of the plan 44, as described in more detail below.

At 44C, the series of boundaries generated by the lesion pattern 50 may be projected back onto the individual CT scan slices, which then may be transferred to a conventional radiosurgical planning tool. Thus, the input to the conventional radiosurgical tool is generally the same as the input in prior methods (i.e., boundaries defined on individual CT scan slices). However, as described in the background of this disclosure, prior methods required a surgeon to draw on each individual slice. In contrast, methods and systems herein generate the input lesion pattern 50 input onto the solid model of the surface 52.

In an embodiment, as described below, a visualization of a dose cloud 54 (right side of FIG. 3) may be provided for displaying on the surface 52. The dose cloud 54 may be received 44D as an output lesion indication by a conventional radiosurgical tool and, in accordance with embodiments, may be displayed 44D, for example, as an isodose contour on the surface 52. As with the lesion pattern 50, the dose cloud 54 may be used in part of generating or approving the plan 44, as described in more detail below.

Figure 4:
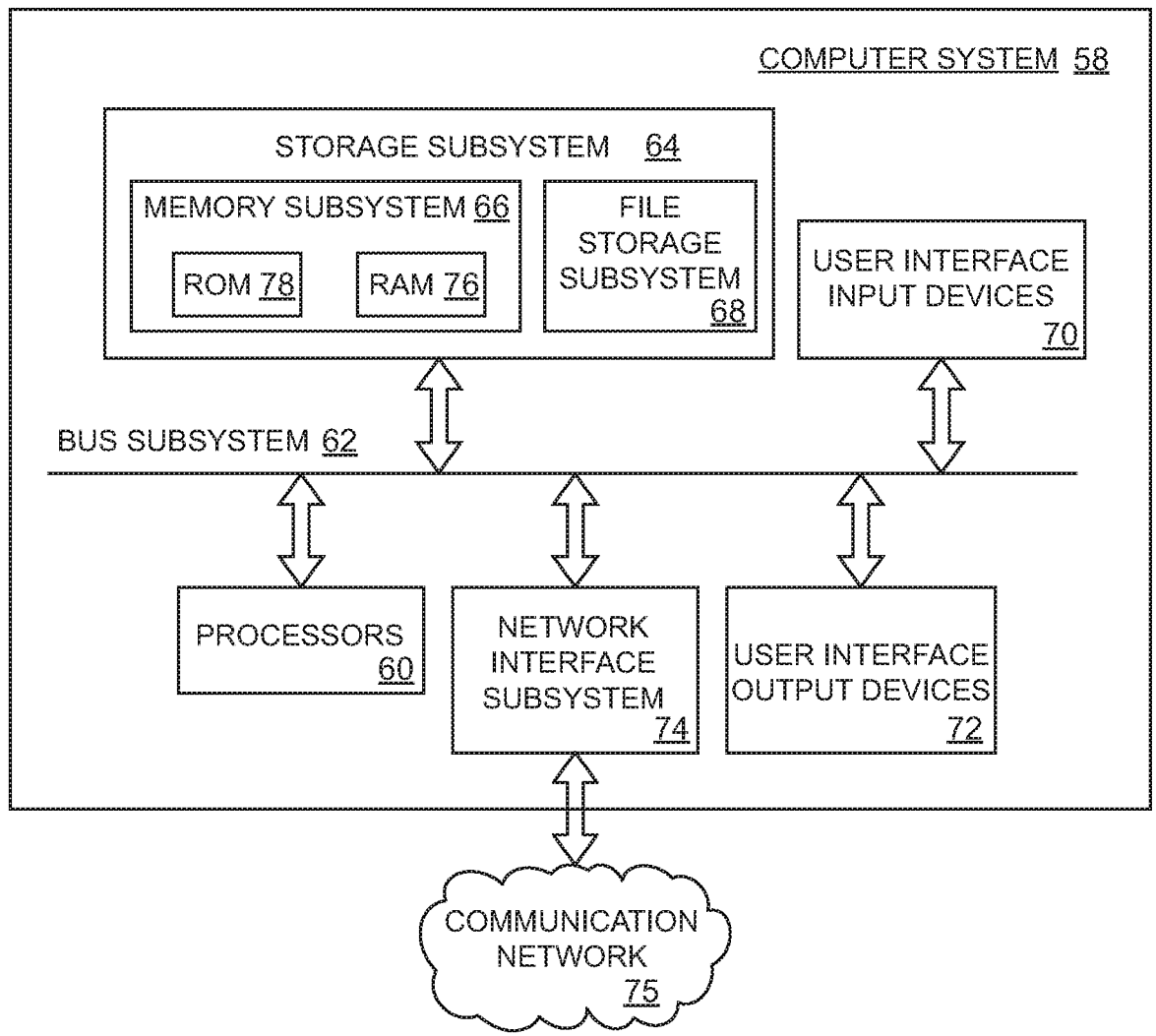
FIG. 4 is a block diagram of a computer system that may be utilized with embodiments herein.

Embodiments herein may utilize computer-implemented methods for generating the surface 52, indicating a desired lesion pattern 50, providing the dose cloud 54, and/or operate the methods or functions of the systems described herein. To this end, FIG. 4 is a simplified block diagram of an exemplary computer system 58 that may be utilized in embodiments described herein. The computer system 58 typically includes at least one processor 60 which communicates with a number of peripheral devices via a bus subsystem 62. These peripheral devices may include a storage subsystem 64, comprising a memory subsystem 66 and a file storage subsystem 68, user interface input devices 70, user interface output devices 72, and a network interface subsystem 74. Network interface subsystem 74 provides an interface to a communication network 75 for communication with other imaging devices, databases, or the like.

The processor 60 performs the operations of the computer system 58 using execution instructions stored in the memory subsystem 66 in conjunction with any data input from an operator. Such data can, for example, be input through user interface input devices 70, such as the graphical user interface. Thus, processor 60 can include an execution area into which execution instructions are loaded from memory. These execution instructions will then cause processor 60 to send commands to the computer system 58. Although described as a "processor" in this disclosure, the functions of the processor may be performed by multiple processors in one computer or distributed over several computers.

User interface input devices 70 may include a keyboard, pointing devices such as a mouse, trackball, touch pad, or graphics tablet, a scanner, foot pedals, a joystick, a touch-screen incorporated into the display, audio input devices such as voice recognition systems, microphones, and other types of input devices. In general, use of the term "input device" is intended to include a variety of conventional and proprietary devices and ways to input information into the computer system. Such input devices will often be used to download a computer executable code from a computer network or a tangible storage media embodying steps or programming instructions for any of the methods of the present invention.

User interface output devices 72 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide non-visual display such as via audio output devices. In general, use of the term "output device" is intended to include a variety of conventional and proprietary devices and ways to output information from the computer system to a user.

Storage subsystem 64 stores the basic programming and data constructs that provide the functionality of the various embodiments. For example, database and modules implementing the functionality of embodiments described herein may be stored in storage subsystem 64. These software modules are generally executed by processor 60. In a distributed environment, the software modules may be stored in a memory of a plurality of computer systems and executed by processors of the plurality of computer systems. Storage subsystem 64 typically comprises memory subsystem 66 and file storage subsystem 68.

Memory subsystem 66 typically includes a number of memories including a main random access memory (RAM) 76 for storage of instructions and data during program execution and a read only memory (ROM) 78 in which fixed instructions are stored. File storage subsystem 68 provides persistent (non-volatile) storage for program and data files, and may include a hard disk drive, a floppy disk drive along with associated removable media, a Compact Digital Read Only Memory (CD-ROM) drive, an optical drive, DVD, CD-R, CD-RW, or removable media cartridges or disks. One or more of the drives may be located at remote locations on other connected computers at other sites coupled to the computer system. The databases and modules implementing the functionality of the present invention may also be stored by file storage subsystem 68.

Bus subsystem 62 provides a mechanism for letting the various components and subsystems of the computer system communicate with each other as intended. The various subsystems and components of the computer system need not be at the same physical location but may be distributed at various locations within a distributed network. Although bus subsystem 62 is shown schematically as a single bus, alternate embodiments of the bus subsystem may utilize multiple busses.

The computer system 58 itself can be of varying types including a personal computer, a portable computer, a workstation, a computer terminal, a network computer, a module in a display unit, a mainframe, or any other data processing system. Due to the ever-changing nature of computers and networks, the description of the computer system 58 depicted in FIG. 4 is intended only as a specific example for purposes of illustrating one embodiment of the present invention. Many other configurations of the computer system are possible having more or fewer components than the computer system 58 depicted in FIG. 4.

Figure 5:
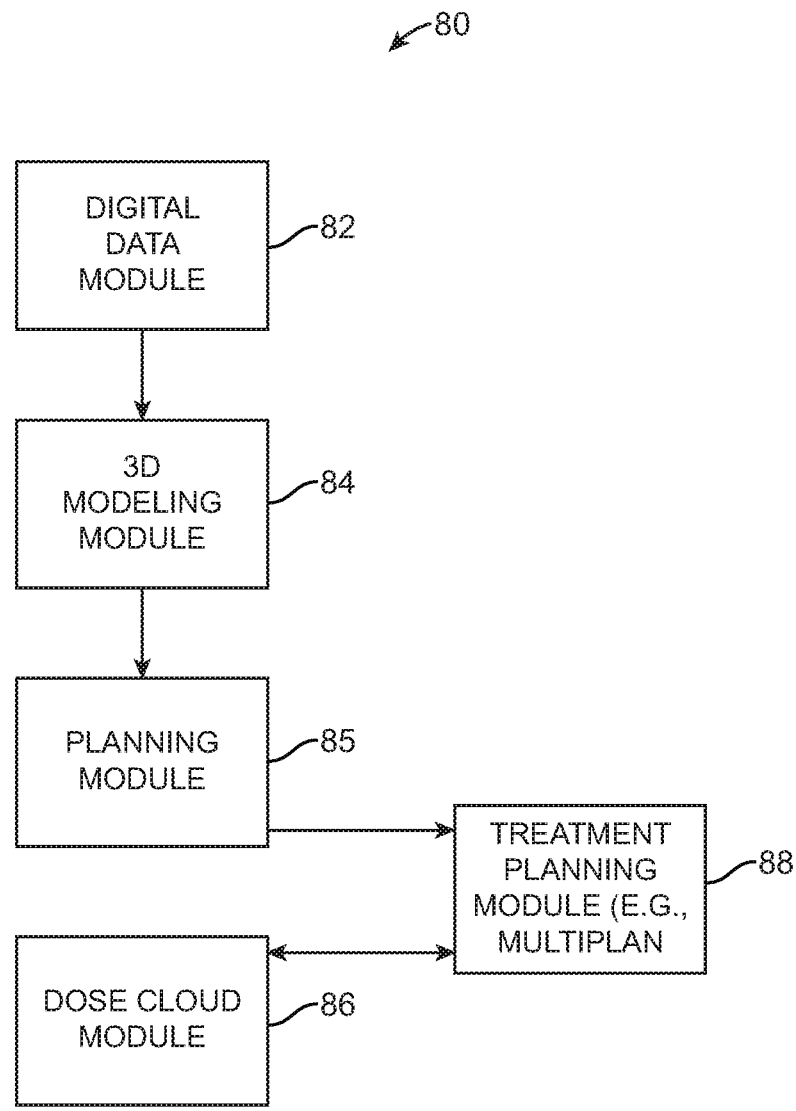
FIG. 5 schematically illustrates a plurality of modules that may carry out embodiments of the present invention.

FIG. 5 schematically illustrates a plurality of modules 80 that may carry out embodiments of the present invention. The modules 80 may be software modules, hardware modules or a combination thereof. If the modules 80 are software modules, the modules will be embodied on a computer readable medium and processed by the processor 60.

A digital data module 82 receives CT volume or other diagnostic images and, if not already digitized, creates a digital data file of the images. A 3-D modeling module 84 builds a finite element or solid model of the desired surface from the digital data file. Such 3-D modeling modules are known, and example implementation details are provided below, along with a description of FIG. 6. However, briefly described, the 3-D modeling module 84 processes the slices of the CT volume and creates a finite element or solid model of the surface of interest, projected as the surface 52 (FIG. 3). For ease of reference, as used from this point forward, the "surface 52" refers to the 3-D model of the surface of interest, and in the embodiments described herein, the inner surface of the heart tissue.

The surface 52 may be shown, for example on a display for the computing device 58, and may be manipulated by a user, for example via the user interface input device 70 so as to see a desired orientation, cross section, or other desired view. Panning and yaw and pitch movement may be provided as well.

A planning module 85 permits a user of the system to generate the lesion pattern 50 (FIG. 3). The planning module 85 may also project the lesion pattern back onto the CT slices.

A dose cloud module 86 may receive or generate the dose cloud 54. An example implementation of the dose cloud module 86 is set forth below, for example with the discussions of FIGS. 18 and 21.

As indicated in FIGS. 3 and 5, the dose cloud module 86 and the 3-D modeling module 84 may be utilized with a standard treatment planning module 88. An example of such a treatment planning module is the MULTIPLAN treatment module, although other treatment modules may be used.

Figure 6:
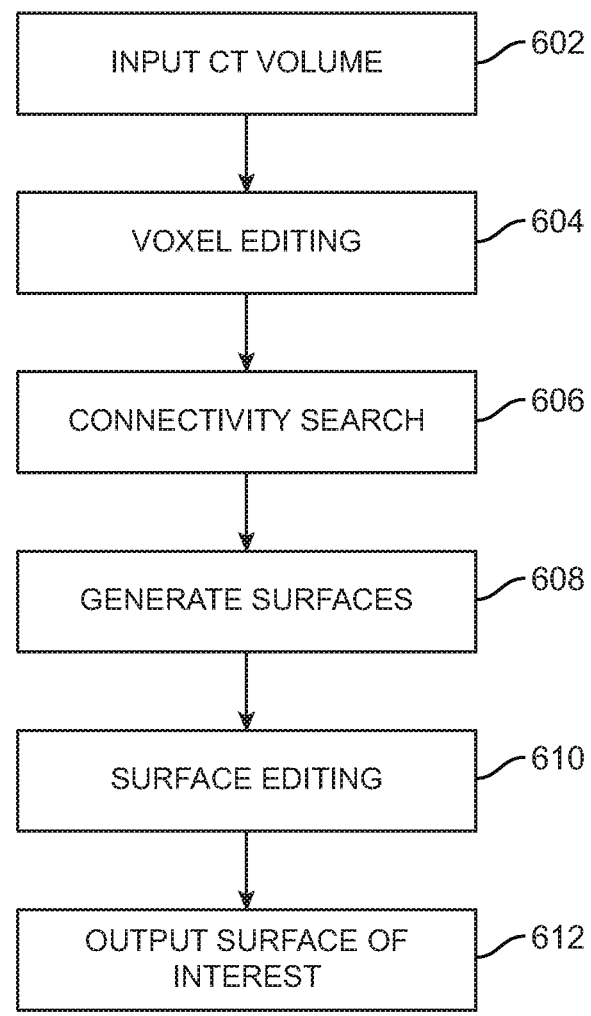
FIG. 6 is a flowchart representing a method of generating a three dimensional model of a surface of interest in accordance with an embodiment.

FIG. 6 is a flowchart representing a method of generating a surface of interest, e.g., the surface 52, in accordance with an embodiment. At 602, the information regarding the CT volume is input, for example via the module 82. This input may be, for example, a CT volume generate to accentuate the tissue-blood boundary information provided for each CT slice. In the examples described herein, the tissue-blood boundary is inner boundary of the heart, and that boundary is accentuated by, for example, adding contrast agent to the blood. The boundary between the blood (including the added contrast) and the heart tissue in each slice of the CT data can be segmented in one, some, or all of the volumetric datasets associated with the cardiac cycle phases. The segmented regions can be stacked or assembled together to form the surface 52. The CT data may be edited, for example to limit the left atrium and the pulmonary veins.

At 604 to 610, examples are provided of smoothing techniques that may be applied between the boundaries of the slices so as to generate a 3-D surface, such as surface 52. Other smoothing techniques may be used. Smoothing may be performed, for example, via the module 84.

At 604, Voxel editing occurs, in which the CT volume is converted to a grid of blocks in three dimensional space. At 606 (optional), connectivity occurs. At 608, surface generation occurs, for example utilizing the Marching Cubes computer graphics algorithm, which proceeds through the voxels, taking eight neighbor locations at a time (thus forming an imaginary cube), then determining the polygon(s) needed to represent the part of the isosurface that passes through the cube. The individual polygons are then fused into the desired surface.

Figure 7:
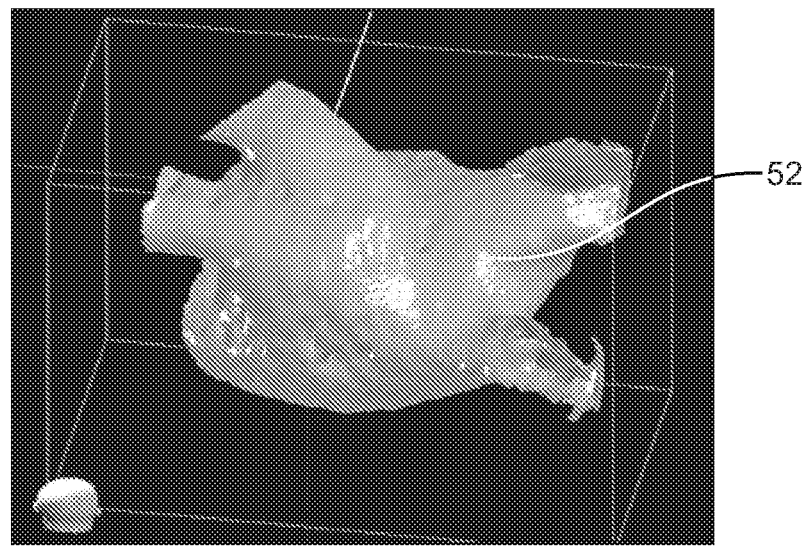
FIG. 7 is a representation of a 3-D model of an inner surface of a heart in accordance with an embodiment.

At 610, the desired surface is output, for example as shown as the surface 52 in FIG. 7. For the example herein, the surface 52 represents the inner surface of the heart. The entire process shown in FIG. 6 may be automated using a segmentation scheme.

Figure 9:
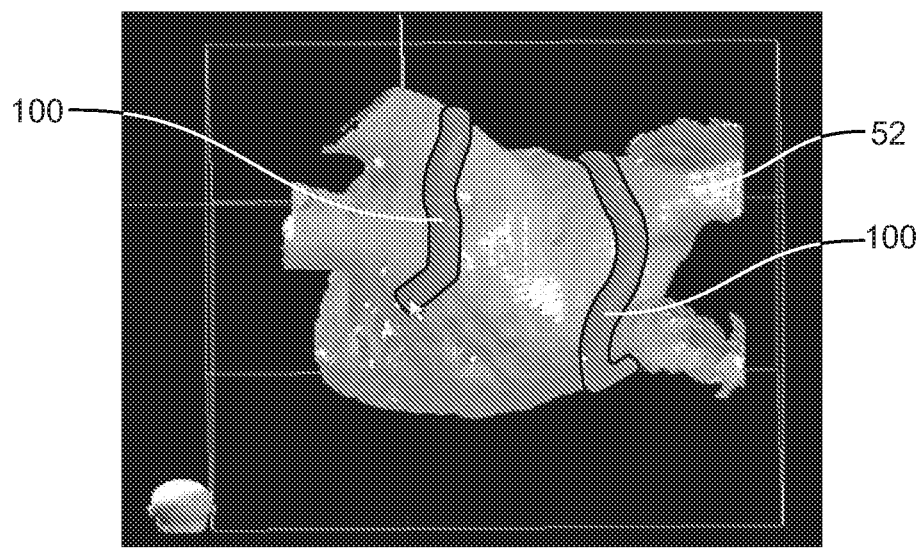
FIG. 9 is a representation of ablation lines 100 being drawn onto the exterior of the surface of FIG. 7 in accordance with an embodiment.
Figure 8:
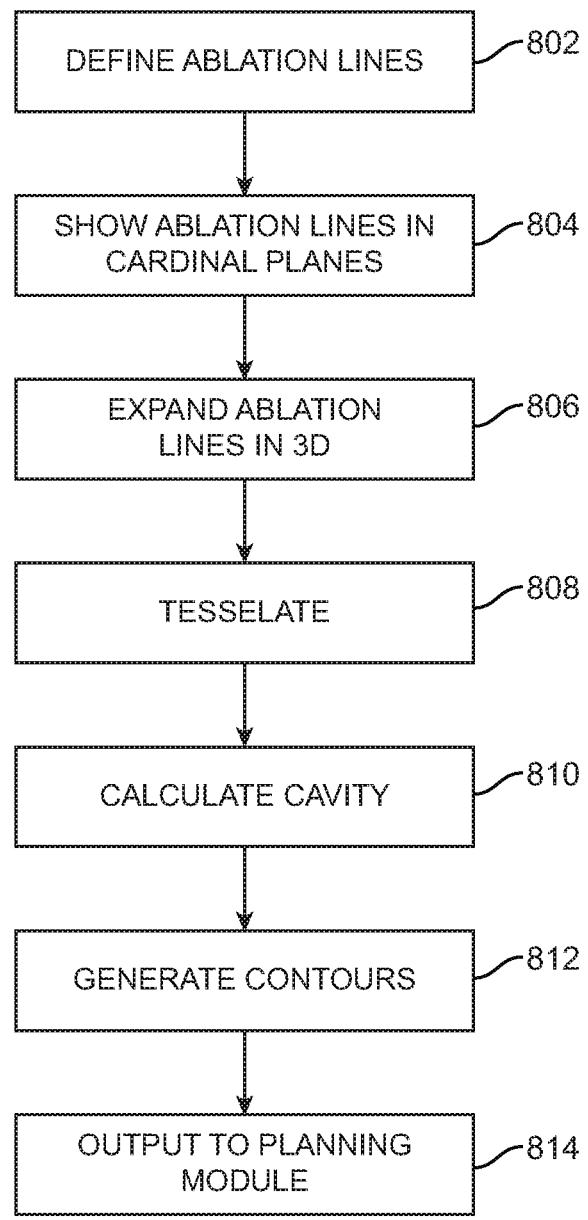
FIG. 8 is a flow chart representing a method for preparing a treatment plan utilizing the model of the surface generated in FIG. 6 in accordance with an embodiment.

FIG. 8 is a flow chart representing a method for preparing a treatment plan utilizing the surface 52 generated in FIG. 6. Beginning at 802, ablation lines 100 (FIG. 9) are defined on the surface 52. For example, the ablation lines 100 may be drawn on or snapped onto the exterior of the surface 52, for example utilizing the user interface input device 70. In an example, a physician may click along the surface and the ablation lines 100 may be extend as a straight line between clicks. Smoothing may be enabled. If desired, the surface 52 may be rotated, panned, and zoomed on the screen, or the pitch or yaw may be altered, so as to allow the physician to access a desired view of the surface to properly orient the ablation lines 100. Such manipulation features are known in existing 3-D modeling and display software.

Applying the ablation lines 100 via the user interface input device 70 allows the planning medical professional to input an appropriate lesion pattern as a series of lines or curves relative to the heart tissue surface 52. The ablation lines 100 may be applied as a very thin line, or as a thickness that is defined by the system or the user. The thickness of the ablation line may be automatically extracted from the 3D data set as well. In accordance with an embodiment, the ablation lines are displayed at a width that is sufficient to prevent propagation of contractions across the lesion. Using such a width provides intuitive visual feedback to a user of the system, so that the user may have a more realistic idea of the location and breadth of a lesion pattern.

Figure 10:
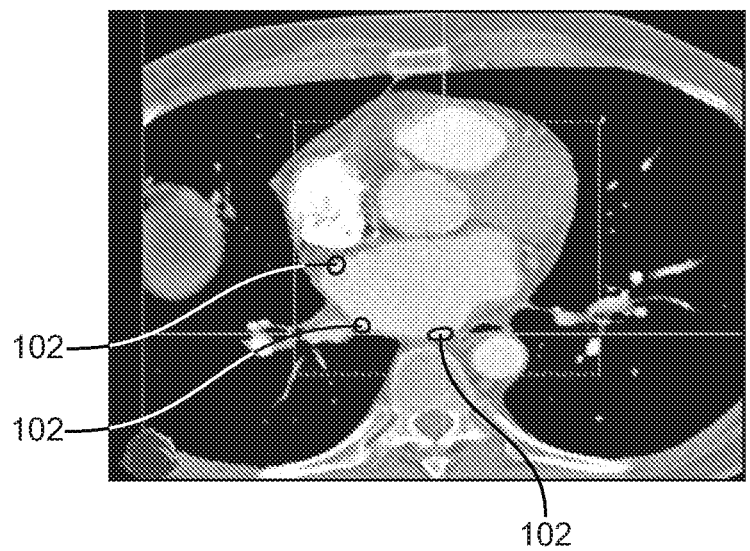
FIG. 10 is a representation of a cardinal plane of the heart for which the surface of FIG. 7 has been generated, showing intersection points of the ablation lines of FIG. 9.

If desired, at 804 the ablation lines may be shown in one or more cardinal planes. As an example, as is shown in FIG. 10, a cardinal plane of the heart for which the surface 52 has been generated shows intersection points 102. The intersection points 102 represent the cross section of the ablation lines 100 at the given cardinal plane. The cardinal planes may be shown either simultaneously on the display, or by toggling between a view of the surface 52 and the cardinal plane. The cardinal planes may represent, for example, data from a single CT slice.

Figure 11:
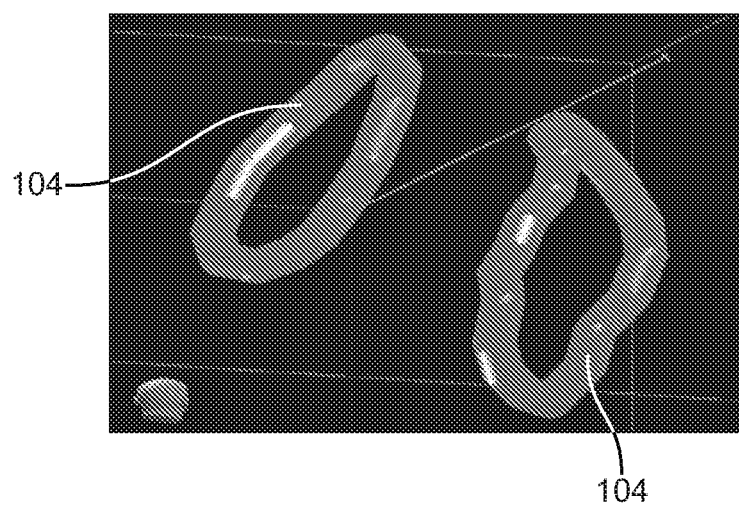
FIG. 11 is a representation of loops generated from the ablation lines of FIG. 9 in accordance with an embodiment.

At 806, the ablation lines 100 are expanded to volumes so as to provide the desired therapeutic benefit, and may be visualized on the display in three dimensions. At 804, the ablation lines shown in cardinal planes may occur after the ablation lines are expanded 806 and indeed, unless stated otherwise herein, the acts set forth in the flowcharts of this disclosure are not limited to the order in which they are presented. To visualize the volume in three dimensions, the ablation lines 100 may be given a three-dimensional thickness, such as by generating loops 104 (FIG. 11). In accordance with an embodiment, since the surface 52 represents an inner surface of the heart, the loops 104 are generated by generating loops having a radius around the ablation lines 100, with the radius being approximately equal to, or slightly more than, the thickness of the tissue to be treated. Thus, the thickness may be sufficient from the inner heart surface for the lesion to extend throughout the heart wall. The radius may be applied around the ablation lines, or separate width and length radii may be used. The width may be selected, for example, to be sufficient to prevent propagation of contractions across the lesion. In an example, the loops 104 may be generated utilizing a radius of two millimeters, but other radii may be used and, as described above, a loop does not necessarily need to be uniform in width and thickness. The thickness of the ablation line may be automatically extracted from the three-dimensional data set as well.

In an embodiment, the loops 104 enclose the pulmonary vein ostia (PVOS) and define a planning target volume (PTV) for treatment planning purposes. The PTV represents the area of tissue of interest at which treatment is desirably to occur. In the example of the heart, the PTV is preferably the tissue of the heart, from the outer surface of the heart to an inner surface, and a width sufficient to inhibiting contractile pathways.

Figure 12:
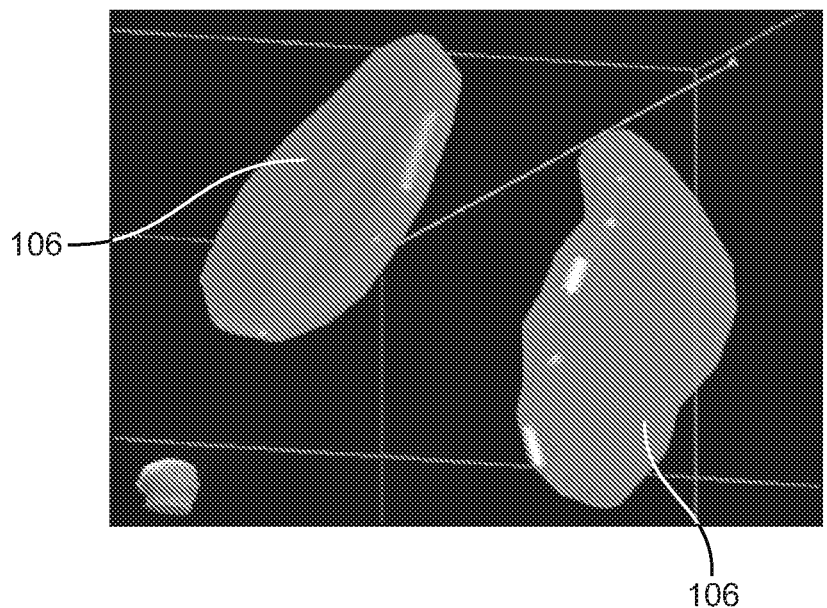
FIG. 12 is a representation of the loops of FIG. 11 tessellated to form solid volumes in accordance with an embodiment.

At 808, the non-planar polygon defined by each loop 104 is tessellated to form solid volumes 106 (FIG. 12). Tessellation may, for example, result in the non-planar polygons being tessellated into triangles, and dilated to the thickness of the ablation line. The solid volumes 106 represent a blood target volume (BTV).

Figure 13:
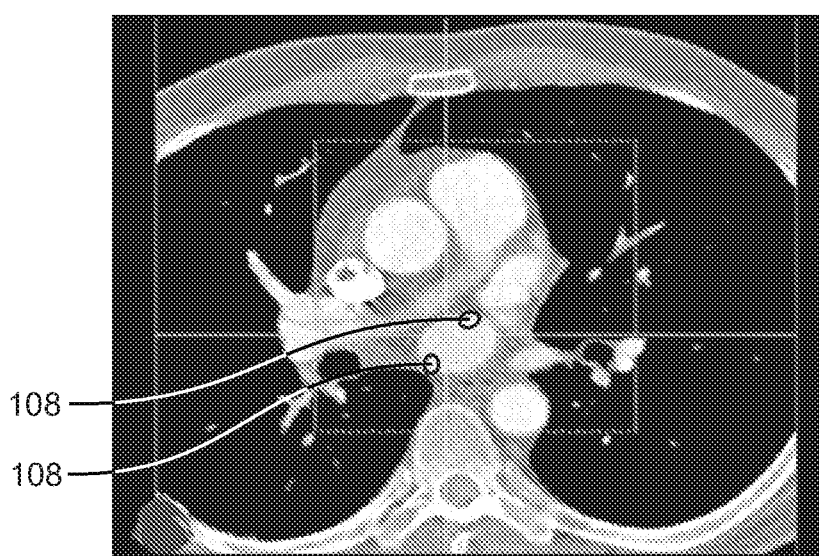
FIG. 13 is an axial slice of the heart with a planning target volume projected thereon in accordance with an embodiment.
Figure 14:
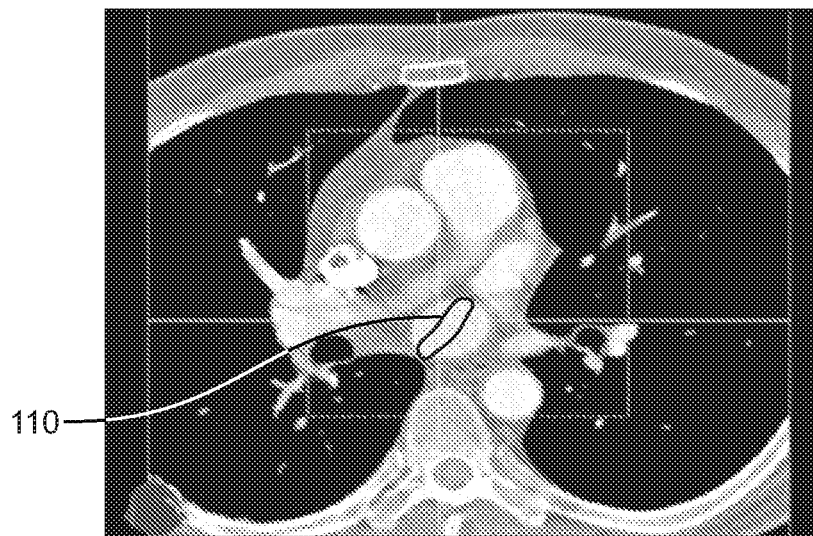
FIG. 14 is the same axial slice as FIG. 13, but shows a blood target volume projected on the heart in accordance with an embodiment.
Figure 15:
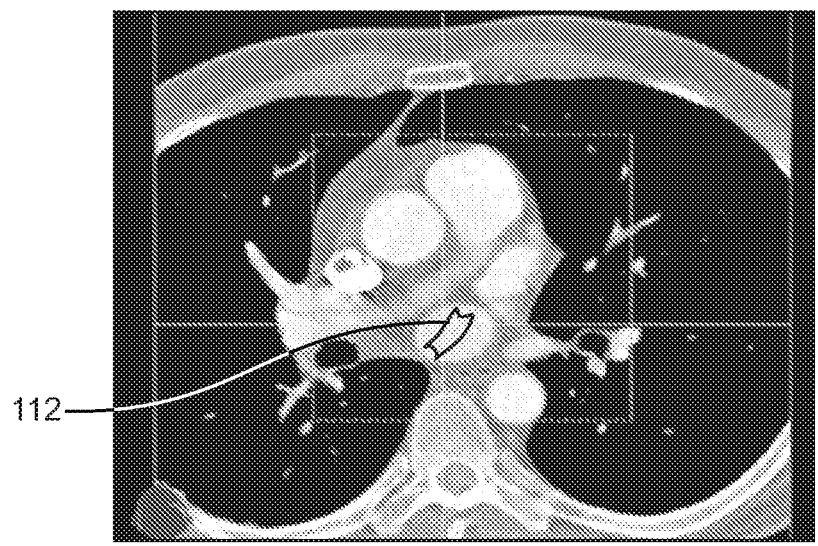
FIG. 15 is the same axial slice as FIG. 13, but shows a cavity projected on the heart in accordance with an embodiment.

FIG. 13 is an axial slice of the heart showing the PTV 108. The PTV 108 in FIG. 13 is shown as two circles, which represent a cross section of the loops 104 formed by the PTV. FIG. 14 is the same axial slice as FIG. 13, but shows the BTV 110. The BTV 110 is represented by the solid volume 106, and includes the desired area of treatment (i.e., the PTV), plus the area in between, which is presumably blood and, in FIG. 14 is represented by an elongated, irregular oval. In general, the blood may be irradiated during treatment without harm, and the treatment plan may be prepared with the assumption that the BTV will be radiated at all locations to an extent sufficient to treat the PTV. At 810, a cavity 112 (shown in axial slice in FIG. 15) is calculated by subtracting the PTV from the BTV. The cavity 112 represents the area of the BTV presumed to be blood.

Figure 16:
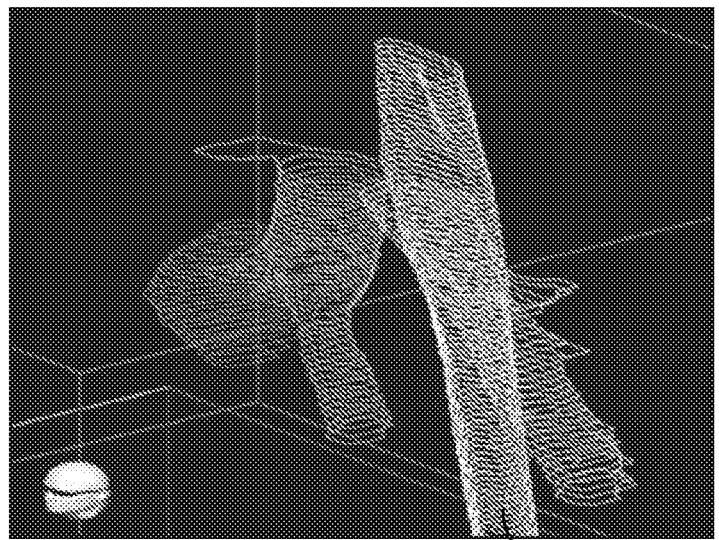
FIG. 16 is a radiation contour distribution showing contours in accordance with an embodiment.
Figure 17:
FIG. 17 is an axial slice of a heart with the contours shown in FIG. 17.

At 812, the PTV and BTV are scan converted to generate contours in each of the cardinal planes. Existing radiosurgical radiation beam calculating modules may be used to determine the resulting radiation contour distribution. Existing radiosurgical planning approaches to identification of radiation sensitive structures may be implemented. The input to such existing calculating modules may require input via slices, such as conventional CT slices. Thus, if such calculating modules are used, the CT slices are utilized to generate the solid volume (FIG. 6), the plan is formed on the solid volume (FIG. 8), and then the plan at each slice is provided back to the calculating module to generate the contours. Thus, the output 814 may be an output relative to each of the original CT slices. An example of generated contours 114 is shown in FIG. 16. An example of an axial slice of the contours 114 is shown in FIG. 17.

Alternatively, the ablation lines 100 may be defined using a cardiac and/or respiratory gated 4DCT data set. Suppose there N (typically N=10) volumes of CT data acquired over time. A heart-wall surface (e.g., the surface 52) will be constructed from each CT volume, resulting in N such surfaces. Using each surface, a set of ablation lines will be defined by the user, resulting in N such ablation lines. This time-varying ablation lines and the time-varying CT data will then be imported to a treatment planning station line treatment planning module, e.g., MULTIPLAN, for generating a treatment plan. Alternatively, one ablation line set, whose volume will include the volumes from all individual ablation lines, can be generated and used for planning.

In accordance with an embodiment, placement of the ablation lines on a surface may be partially or fully automated. A template of possible ablation lines may be provided to the user, and the user may then drag and drop the selected template at a proper location on the surface. The user may modify the ablation line locally by moving it around on the surface. The thickness may also be changed.

The contours 114 may be saved, for example, as DICOM RTSS (Radiation Therapy Structure Sets) files. The planner to which they are output may be, for example, MULTIPLAN. In an embodiment, optimization in MULTIPLAN is done using the BTV, while evaluation is done using PTV. The volume of the BTV in general is significantly larger than the PTV. The BTV is also a shape topologically closer to a sphere than the PTV, which is topologically closer to a hole, which is formed by the radiation pattern. Because of these reasons, implementing a treatment plan based on the BTV is preferred. Optimizing the plan based on the PTV is preferred because focus is on the actual area in which treatment is desired.

In another embodiment, instead of transmitting the ablation lines as 2D contours in cardinal planes or oblique planes to a planning module, the ablation lines may be transmitted as 3D shapes to the planning module.

Along with inputting a desired lesion pattern, as schematically illustrated on the right side of FIG. 5, the planning module and user interface will preferably output an estimate of the actual radiation exposure along the surface of a heart, preferably in the form of an estimated heart surface lesion 54. Estimated lesion 54 may represent the portion of heart tissue surface 52 which receives a radiation dose above a necrotic threshold, optionally based on radiation beams and radiation dose output from an existing radiosurgical treatment planner. Alternative patterns may represent an estimate of tissue which will receive a sufficient dose of radiation for therapeutic remodeling so as to inhibit the arrhythmia. The user may interactively develop the plan based on iterative input into and output from the planning treatment module 88.

Ideally, the dose cloud should correspond to the ablation lines. Embodiments herein strive to create a plan that provides treatment as an ring of fibrotic tissue corresponding to ablation lines.

Figure 18:
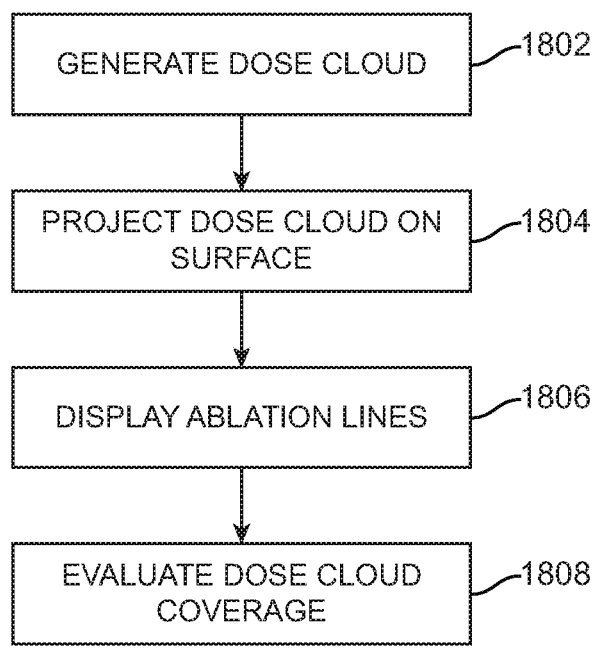
FIG. 18 is a flow chart representing a method of evaluating a dose cloud with respect to the generated surface in accordance with an embodiment.

FIG. 18 is a flow chart representing a method of evaluating a dose cloud with respect to the generated surface 52 in accordance with an embodiment. At 1802, the dose cloud is generated and is overlaid over the surface 52 at 1804. If desired, the ablation lines 100 are displayed on the surface 52 at 1806.

Figure 19:
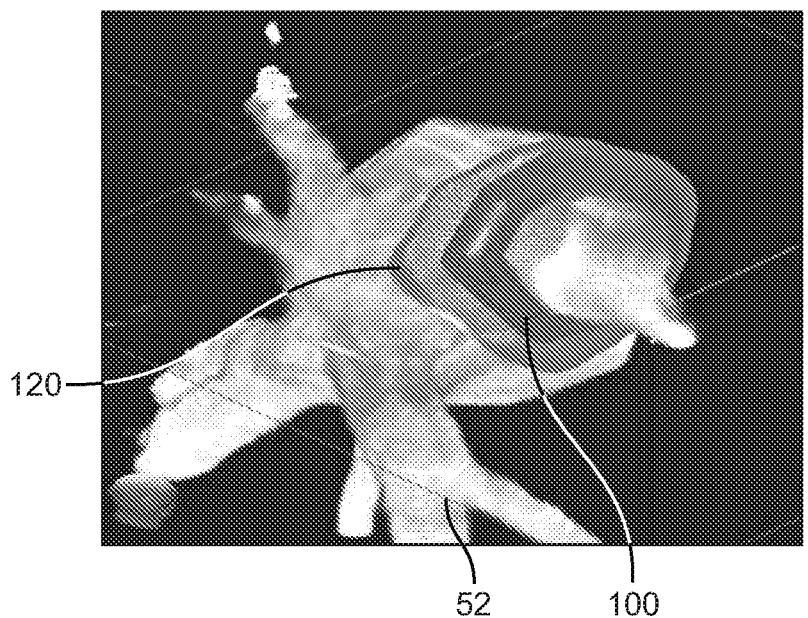
FIG. 19 shows a dose cloud projected on the generated surface along with ablation lines in accordance with an embodiment.

As shown in FIG. 19, displaying the ablation lines 100 and a dose cloud 120 relative to the surface 52 allows a visual inspection of whether the dose cloud is covering the target intended by the physician. To this end, at 1808, the physician may visually evaluate whether the dose cloud is covering the target. As can be seen in FIG. 19, for at least the view shown in the drawing, the dose cloud 120 fully covers the ablation lines 100. Rotation, panning, or zooming of the surface, or adjustment of the pitch and/or yaw, may be required for a full inspection of dosage coverage.

Figure 20:
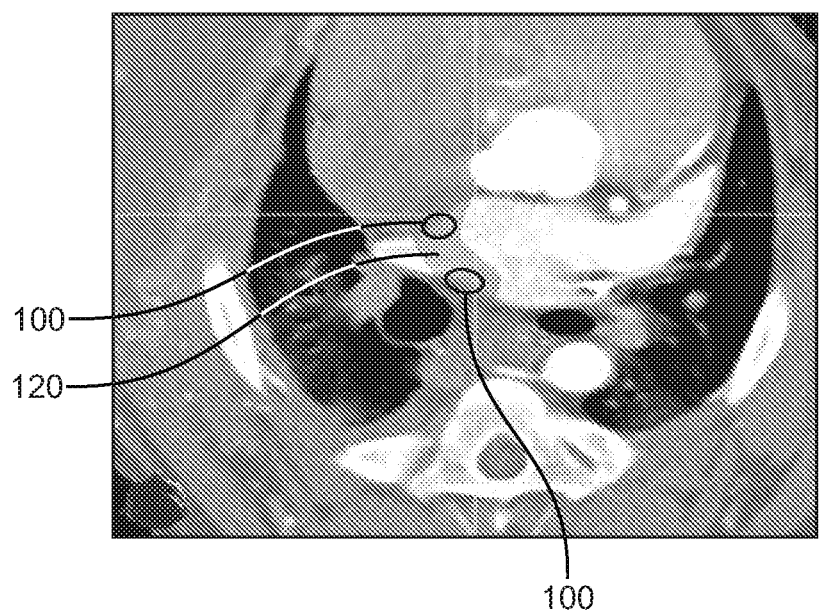
FIG. 20 is an axial slice of the generated surface of FIG. 19, with the dose cloud and the ablation lines shown thereon.

The dose cloud 120 may represent, for example, all dose values that are greater than a particular threshold or, as an alternative, dose values lying in a range between a minimum and a maximum. If desired, as shown in FIG. 20, an axial slice of each cardinal plane may be provided, with the dose cloud 120 and the ablation lines 100 shown thereon. This representation permits a physician to look at each slice to ensure that the dose is covering (e.g., surrounding) the target adequately.

Figure 21:
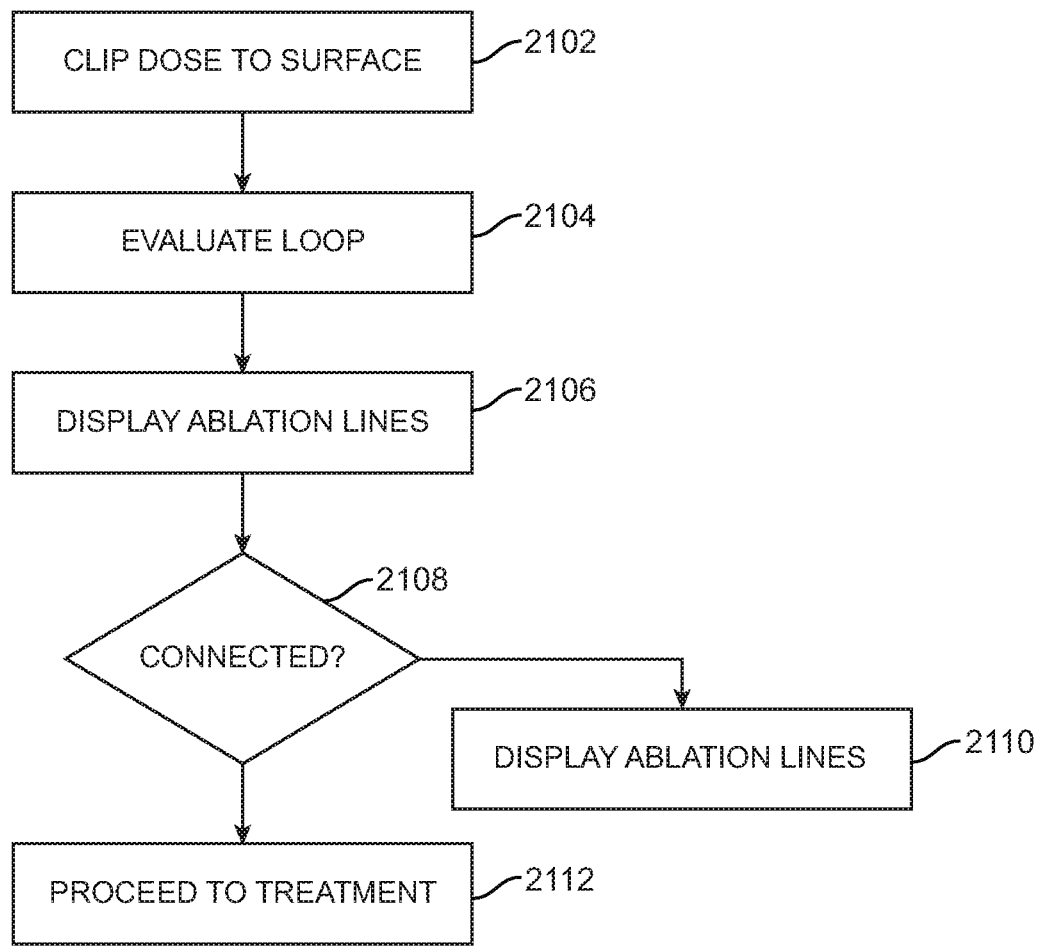
FIG. 21 is a flow chart representing a method of determining if a dose is sufficient in accordance with an embodiment.

FIG. 21 is a flow chart representing a method of determining if a dose is sufficient in accordance with an alternate embodiment. The method in FIG. 21 involves clipping a dose cloud to the surface 52, and may be used in addition to, or instead of the visual inspection described above, where the dose cloud is represented more as a contour. At 2102, the region corresponding to the acceptable dose value is clipped to the surface 52, for example as a different color than the ablation lines 100. The dose values may be represented in isodose fashion, with different doses being displayed in different ways, for example as different colors. Alternatively, as in the previous embodiment, all doses exceeding a value or falling in a range may be displayed.

Figure 22:
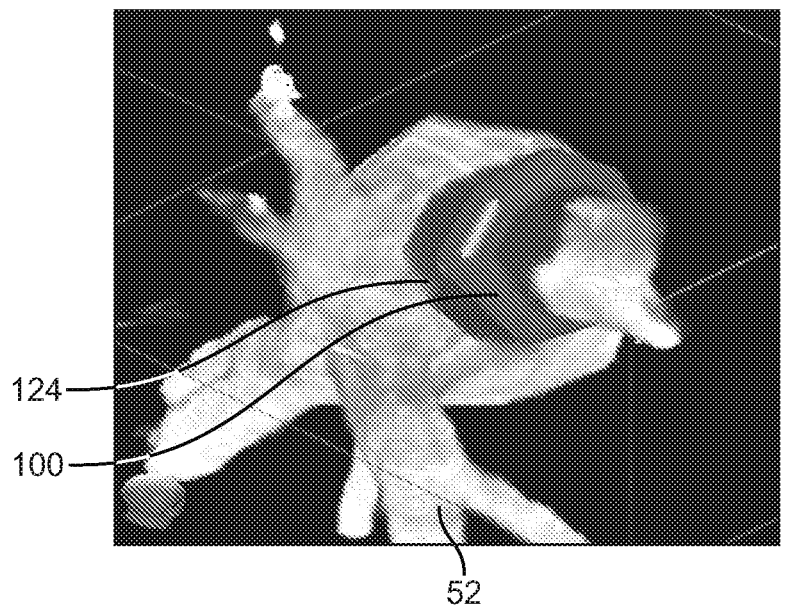
FIG. 22 shows a surface patch indicating dosage coverage on a generated tissue surface in accordance with an embodiment.

By clipping the dose value to a surface, the dose is presented as a curved surface patch 124 (FIG. 22) on the surface 52. If the dosage values are selected correctly, fibrosis should take place on the surface patch 124. A physician may visually evaluate the surface patch 124 with respect to the ablation lines 100 to determine whether sufficient dosage is provided. For example, the surface patch may be evaluated to determine whether it is wide enough to inhibit contractile pathways in the tissues being treated.

In addition, with or without the ablation lines 100 removed, the physician may evaluate the surface patch 124 to determine whether the surface patch forms a continuous loop at 2104. If there are any breaks in the loop, inhibiting contractile pathways may not be provided by the radiological treatment. To this end, at 2106, the physician evaluates whether the surface patch 124 is connected around the surface 52, such that a continuous loop is formed. If not, an error may be generated at 2108, either by software or a recognition by the user, causing the physician to construct a new plan or causing the computer system 58 to generate an error message, or to be handled in another manner. If the loop is connected, then the physician may proceed to treatment at 2110.

Figure 23:
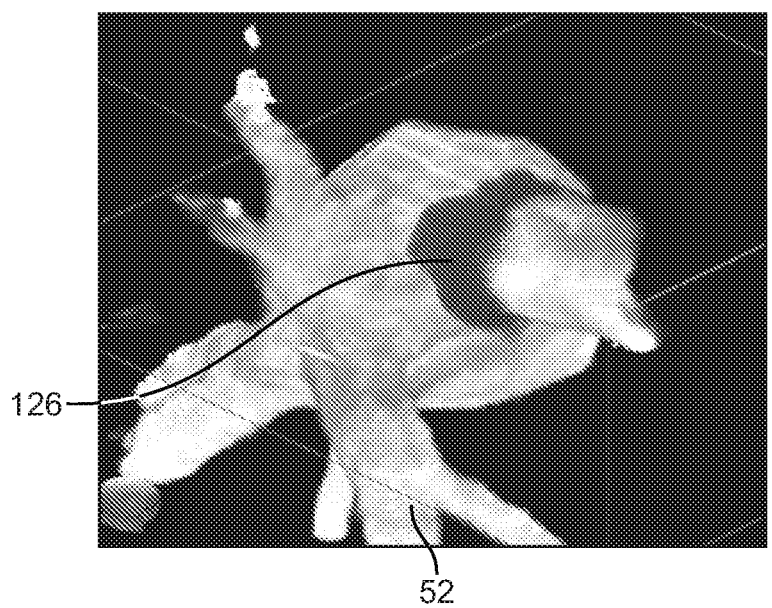
FIG. 23 shows a generated surface in which a loop of the dosage surface patch is complete around the generated surface.

FIG. 23 shows the surface 52 in which a complete loop 126 around the surface 52 is formed by the surface patch 124. The physician and/or the computer system 58 may rotate and otherwise manipulate the surface 52 so that the physician may fully inspect the loop 126. In an alternate embodiment, software may walk across the loop 126 to confirm that the loop returns to a starting position to make sure that the fibrotic region is connected. This same software or visual inspection may be used to determine whether the loop is sufficiently wide around the entire loop 126. For example, the software may crawl around the surface 52, and evaluate a pixel width of the loop 126. If the pixel width falls below a threshold, an error may be generated.

Any effects of possible misalignment errors (x, y, z translation and roll, pitch, yaw, rotation errors) during treatment may be evaluated with this system. The surface or the CT data set may be translated and rotated in relation to the dose cloud to understand the effect of any misalignment on the continuity of the fibrotic loop at the PVOS. Alternatively the dose cloud may be translated or rotated in relation to the surface or the CT data set.

Figure 24:
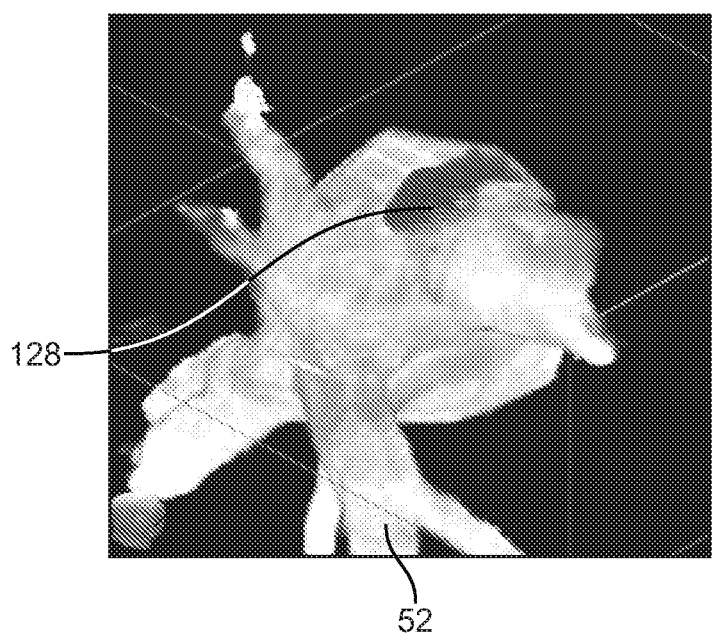
FIG. 24 shows a generated surface in which a loop of the dosage surface patch is not complete around the generated surface.

FIG. 24 shows a partial loop 128 that does not extend entirely around the surface 52. In this example, the physician or the software may require that a new treatment plan be prepared or may otherwise generate an error (e.g., at 2108).

After the contours are approved, the plan 44 is complete, and may be implemented. Radiosurgical treatment of the heart 46 may be initiated, for example, by positioning the patient on patient support 24, bringing the patient into alignment with robot arm 14, and directing the planned series of radiation beams from the linear accelerator 12 to the target region of the heart.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A radiosurgical method for treating a patient body having a heart, the heart having a non-tumerous disease, the method comprising:
   acquiring three-dimensional image data from the heart;
   generating a three-dimensional model of a tissue surface of the heart utilizing the image data;
   receiving user input on the surface model of a desired ionizing radiation treatment lesion pattern for mitigating the disease; and
   outputting information regarding a planned lesion pattern relative to the three-dimensional image data based upon the desired lesion pattern.

2. The method of claim 1, wherein generating the three-dimensional model comprises generating a model of the heart based upon a boundary between blood and tissue of the heart.

3. The method of claim 2, wherein the boundary comprises an inner surface of the heart tissue.

4. The method of claim 2, wherein the three-dimensional image data from the heart comprises a plurality of slices of two-dimensional data, and wherein generating the three-dimensional model comprises generating a model of the heart based upon segments of the boundary between the blood and the heart tissue in each slice of the two dimensional data.

5. The method of claim 4, wherein the three-dimensional model is formed by stacking or assembling together the segments, and by extending the surface between the segments.

6. The method of claim 4, wherein outputting comprises projecting the lesion pattern onto each of the plurality of slices of two-dimensional data.

7. The method of claim 1, wherein the three-dimensional image data from the heart comprises a plurality of slices of two-dimensional data, and wherein outputting comprises projecting the lesion pattern onto each of the plurality of slices of two-dimensional data.

8. The method of claim 1, further comprising generating a three-dimensional volume for a lesion based upon the user input, and generating the information based upon the three-dimensional volume.

9. The method of claim 8, wherein generating the volume comprises expanding the user input to a width that is sufficient to inhibit contractile pathways.

10. The method of claim 8, wherein generating the volume comprises expanding the user input to a depth that is sufficient to transmurally penetrate through the tissue of the heart.

11. The method of claim 8, wherein generating the volume comprises expanding the user input to cover an area of tissue of interest at which the treatment is to occur.

12. The method of claim 1, further comprising generating an ionizing radiation treatment plan based upon the information, and projecting a dose cloud to the solid model based upon the treatment plan.

13. The method of claim 12, further comprising snapping the user input on the lesion pattern to the surface of the model.

14. The method of claim 13, further comprising evaluating the dose cloud with respect to the user input to determine sufficient treatment.

15. The method of claim 14, wherein evaluating comprises walking the dose cloud around the surface to confirm that the loop forms an enclosed perimeter around the surface.

16. The method of claim 15, wherein walking comprises evaluating a thickness of the loop with respect to a threshold.

17. A radiosurgical method for treating a patient body having a heart, the heart having a non-tumerous disease, the method comprising:
acquiring three-dimensional image data from the heart;
generating a three-dimensional model of a tissue surface of the heart utilizing the image data;
receiving user input on the surface model of a desired ionizing radiation treatment lesion pattern for mitigating the disease; and
generating an ionizing radiation treatment plan based upon the desired lesion pattern, and projecting a dose cloud relative to the image data based upon the desired treatment plan.

18. The method of claim 17, further comprising snapping the user input for the lesion pattern to the surface of the model.

19. A radiosurgical system for treating a patient body with a heart, the heart having a non-tumerous disease, the system comprising:
an image capture device for acquiring three-dimensional planning image data from the heart; and
a processor system comprising a modeling module coupled to the image data for generating a surface model of the heart based upon the image data, and an input for identifying a target region of the heart on the surface model, the processor system coupling the input to the modeling module so as to generate a lesion pattern on the image data in response to the input on the surface model.

20. The apparatus of claim 19, wherein the modeling module is configured to generate the three-dimensional model of the heart based upon a boundary between blood and tissue of the heart.

21. A method for determining one or more cardiac arrhythmia targets for ablation, the method comprising:
receiving a first set of image data;
receiving an indication of an abnormality in a second set of image data; and
defining the one or more cardiac arrhythmia targets based on the first and second sets of image data; wherein defining the one or more cardiac arrhythmia targets includes determining a dose pattern within and around the target.

22. A computer-implemented method for identifying cardiac arrhythmia targets, the method comprising:
receiving three-dimensional image data from the heart of a patient;
receiving a user input related to desired lesion; and
forming, based on the three-dimensional image data from the heart of the patient and the received user input, a model of a three-dimensional lesion; wherein forming the model of the three-dimensional lesion comprises determining a dose pattern within and around the lesion.

* * * * *